United States Patent
Boling

(10) Patent No.: US 6,597,953 B2
(45) Date of Patent: Jul. 22, 2003

(54) FURCATED SENSING AND STIMULATION LEAD

(75) Inventor: C. Lance Boling, San Jose, CA (US)

(73) Assignee: NeuroPace, Inc., Mountain View, CA (US)

( * ) Notice: Subject to any disclaimer, the term of this patent is extended or adjusted under 35 U.S.C. 154(b) by 59 days.

(21) Appl. No.: 09/789,171

(22) Filed: Feb. 20, 2001

(65) Prior Publication Data

US 2002/0116042 A1 Aug. 22, 2002

(51) Int. Cl.[7] .................................................. A61N 1/08
(52) U.S. Cl. ......................................... 607/45; 607/122
(58) Field of Search ............................ 607/45, 122, 46; 600/554

(56) References Cited

U.S. PATENT DOCUMENTS

| | | | | |
|---|---|---|---|---|
| 5,335,657 A | * | 8/1994 | Terry, Jr. et al. | 607/45 |
| 5,782,798 A | * | 7/1998 | Rise | 604/500 |
| 5,984,909 A | * | 11/1999 | Lurie et al. | 600/374 |
| 6,016,449 A | * | 1/2000 | Fischell et al. | 607/45 |
| 6,018,682 A | * | 1/2000 | Rise | 607/45 |
| 6,128,537 A | * | 10/2000 | Rise | 128/898 |
| 6,141,593 A | * | 10/2000 | Patag | 607/122 |
| 6,192,280 B1 | * | 2/2001 | Sommer et al. | 607/122 |

* cited by examiner

*Primary Examiner*—Alfred Basichas

(57) ABSTRACT

A furcated medical electrical lead for neurological applications has a distal portion having a plurality of distal end segments, each of which bears at least one distal electrode for electrographic sensing or electrical stimulation. The furcated configuration allows each distal end segment to be implanted in a different site in the patient's brain. In contrast to surface strip or grid electrodes, shallow implantation reduces the probability that any of the electrodes will move away from the surface of the brain due to atrophy or other phenomena.

36 Claims, 5 Drawing Sheets

FURCATED SENSING AND STIMULATION LEAD

FIELD OF THE INVENTION

The invention is related to implantable medical leads, and more particularly to implantable cortical electrical leads used to sense electrographic signals from a patient's brain or to apply electrical stimulation to the brain.

BACKGROUND OF THE INVENTION

In the medical diagnosis and treatment of various brain disorders, including epilepsy, Parkinson's disease, sleep disorders, and psychiatric ailments, it is customary and frequently useful to analyze electrical signals originating in the brain. For a review of this technology, see Ajmone-Marsan, C., Electrocorticography: Historical Comments on its Development and the Evolution of its Practical Applications, *Electroencephalogr. Clin. Neurophysiol. Suppl.* 1998, 48:10–16; there are numerous other applications. These electrographic signals are commonly known as electroencephalogram (EEG) signals when originating or received at the surface of the brain, such as from scalp electrodes, or electrocorticogram (ECoG) signals when originating or received below the surface of the brain, such as from intracranial electrodes. The term "EEG" will be used generically herein to refer to both types of signals.

It is also becoming accepted to apply electrical stimulation to various structures of the brain for both diagnostic and therapeutic purposes. For an exemplary diagnostic application, see Black, P. M. & Ronner S. F., Cortical Mapping for Defining the Limits of Tumor Resection, *Neurosurgery* 1987, 20:914–919, which addresses the use of electrical stimulation via deep brain electrodes to identify functional portions of the brain prior to and as a planning stage in surgical resection. For an example of a therapeutic application, see Cooper, I. S. & Upton, A. R. M., Effects of Cerebellar Stimulation on Epilepsy, the EEG and Cerebral Palsy in Man, *Electroencephalogr. Clin. Neurophysiol. Suppl.* 1978, 34:349–354. In both of these examples, acutely implanted brain electrodes are connected to external equipment.

It is also contemplated that chronic electrical stimulation can be used as a direct treatment for disorders such as epilepsy. See, e.g., U.S. Pat. No. 6,016,449 to Fischell, et al., which describes an implantable neurostimulator that is coupled to relatively permanent deep brain electrodes.

Although it is frequently possible to employ scalp electrodes for certain types of EEG monitoring and analysis, it has been found that ambient electrical noise (such as from the 50/60 Hz power system) can adversely impact signal-to-noise ratio, and certain signal components of interest may be filtered out by the patient's intervening cranium and scalp tissue. Moreover, precise localization is less feasible with scalp electrodes.

Accordingly, intracranial signal analysis, that is, the consideration of signals that originate from within a patient's cranium, whether by internal or external apparatus, is best accomplished with brain surface electrodes, such as strip and grid electrodes, cortical depth leads, or some combination of surface electrodes and depth leads.

Typical brain surface strip and grid electrode arrays consist of flat, disk-shaped electrodes that are placed on the surface of the patient's brain. In a typical strip or grid electrode array, each electrode has an exposed diameter of approximately 3 mm (or ⅛ inch), and the electrodes are distributed along a line (for a strip electrode array) or in a rectangular grid (for a grid electrode array) at a pitch of approximately 10 mm.

Unfortunately, brain surface strip and grid electrode arrays have a tendency, particularly with long-term chronic use, to move away from the surface of the brain. This can be caused by atrophy or other mechanisms associated with cerebrospinal fluid (CSF) dynamics. The result is frequently unsatisfactory or intermittent electrical contact between the electrodes and the desired brain tissue. It frequently requires further surgery (with the associated risks for the patient) or electronic compensation for the change in characteristics (with a potentially harmful increase in stimulation current being delivered to the brain, or at minimum, decreased signal-to-noise ratio), and may result in long-term performance deterioration. There is no known acceptable way to anchor a traditional strip or grid electrode array to the surface of the brain. While the electrode may be anchored to the patient's cranium or dura mater, the brain tends to recede from these structures in certain cases. Moreover, the electrodes are spaced evenly along a line or grid, and while it is possible to orient a strip or grid electrode array in a desired manner, it is generally not possible to position the individual electrodes independently.

Typical brain depth leads are flexible small-diameter (usually 1–1.5 mm) round leads having distal electrodes. It is known for depth leads to have multiple independent distal electrodes on the same lead shaft, but such electrodes are generally located coaxially along a distal portion of the shaft. It is difficult, and usually impractical, to attempt to position the individual electrodes independently.

Accordingly, it would be desirable to have an implantable medical electrical lead that provides the advantages of both surface electrodes and depth leads, along with other advantages. Such an electrical lead would have multiple distal electrodes that are independently positionable near the surface of the brain or in deep brain structures, and would remain in contact with the desired neural tissue regardless of atrophy or other adverse conditions.

SUMMARY OF THE INVENTION

A medical electrical lead in accordance with the present invention has a furcated, or split, distal portion with two or more separate end segments, each of which bears at least one sensing or stimulation electrode. The end segments are individually positionable and narrow in diameter, and in various configurations may be used as depth leads or positioned near the surface of the brain to operate in a manner similar to surface electrodes. In either case, the distal tips of the end segments are anchored in brain tissue, either in deep brain structures or near the surface, as desired by the treating practitioner. Accordingly, in comparison to traditional strip and grid electrode arrays, there is less likelihood that atrophy or other physiological mechanisms will cause the electrodes to dislodge from the cortex.

A furcated lead according to the invention is preferably provided with an inline lead connector area at its proximal end, to maintain compatibility with known, existing, and improved inline lead connectors. Inline lead connectors tend to be the smallest and easiest to operate type of lead connectors, both important characteristics, especially in the surgical and implantable arenas.

With leads in accordance with the present invention, it is possible to realize several additional advantages. With plural individually positionable distal electrodes, it is possible to reach a larger number of separate brain sites while limiting the number of leads necessary to do so. The number of leads connected to an external apparatus or implanted neurostimulator (or other device) is minimized, thereby improving the ease of treating the patient, improving ease of lead management, reducing the possibility of lead breakage, and reducing the possibility of discomfort or erosion under the patient's scalp.

BRIEF DESCRIPTION OF THE DRAWINGS

These and other objects, features, and advantages of the invention will become apparent from the detailed description below and the accompanying drawings, in which.

DETAILED DESCRIPTION OF THE INVENTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

Figure 1:
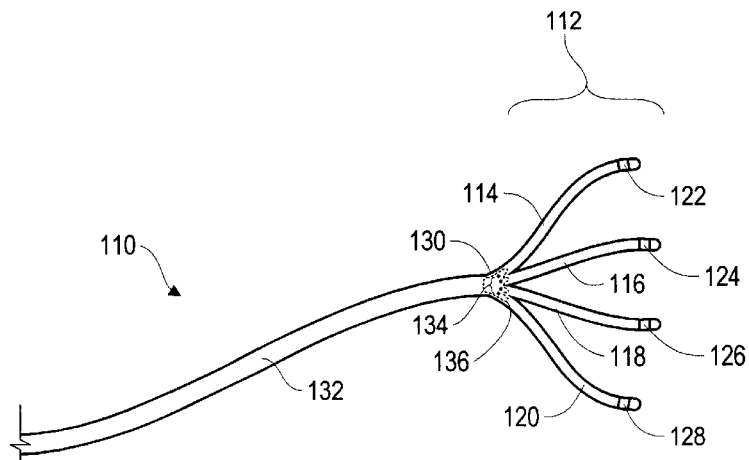
FIG. 1 is an exemplary distal portion of a furcated lead according to the invention.

Referring initially to FIG. 1, an exemplary distal portion 112 of a furcated medical electrical lead 110 is illustrated. The illustrated embodiment has four distal end segments 114, 116, 118, and 120, each of which has a corresponding electrode 122, 124, 126, and 128 near the tip. The distal end segments 114–120 are symmetric and arranged in a substantially two-dimensional fan-like configuration as illustrated in FIG. 1, but it will be appreciated that numerous alternative configurations, such as three-dimensional radial configurations and numerous others, are possible and may be advantageous in the context of the present invention, as set forth below.

As shown, the lead 110 is flexible, and as described in further detail below, is fabricated primarily from a biocompatible elastomer such as silicone, urethane, or any of a number of suitable biocompatible materials, with internal conductors extending between the electrodes 122–128 and a lead connector area (not shown) at a proximal end of the lead 110. Each of the distal end segments 114–120 is similarly constructed and flexible, and accordingly, it may be difficult in certain situations to guide the distal end segments 114–120 into the patient's brain tissue. To address this potential limitation, a junction area 130 between a body portion 132 of the lead 110 and the distal end segments 114–120 is optionally provided with a plurality of stylet holes 134, one for each distal end segment, facilitating electrode placement.

Each of the stylet holes 134 is in communication with a lumen defined by one of the distal end segments 114–120, allowing a stylet to be inserted into the lead 110 to extend through one of the distal end segments 114–120, providing a temporary measure of rigidity to assist in placement. The use of a stylet to implant brain electrodes is well known in the art. Each of the distal end segments 114–120 can be positioned independently in this manner.

Each of the stylet holes 134 is preferably formed as a self-closing septum in the junction area 130, to keep most fluids and other foreign materials out of the interior of the lead 110 when no stylet is in place. Although an implantable lead according to the invention should be able to tolerate some leakage and penetration of bodily fluids when chronically implanted, it is advantageous to provide this structure to avoid excessive contamination. Although the stylet holes 134 are preferably located at the junction area 130, in an alternative embodiment, each of the stylet holes 134 may be located at a desired point along the distal end segments 114–120.

Traditional deep brain leads are frequently positioned in a desired deep brain structure with the assistance of a cannula, a rigid tunneling and positioning tool capable of sliding over the shaft of a brain electrode. The cannula is retracted once the cannula (and the lead inside) is appropriately placed. It should be noted that a lead according to the invention does not need and is advantageously used without a cannula for several reasons. In particular, it should be noted that the entire lead 110 typically is not embedded in the brain, only the distal end segments 114–120 are. These segments are extremely narrow in diameter, on the order of 0.5 mm (see below), and are very easy to position either shallow or relatively deep in the brain without a cannula. Moreover, because of the manner in which the various distal end segments 114–120 attach to the body 132 of the lead 110 via a junction area 130, it is generally impracticable to position the distal end segments 114–120 independently with a cannula (or cannulae) of any traditional kind—a cannula would not be retractable over the junction area 130 without affecting the positioning of other, previously inserted, distal end segments.

Figure 8:
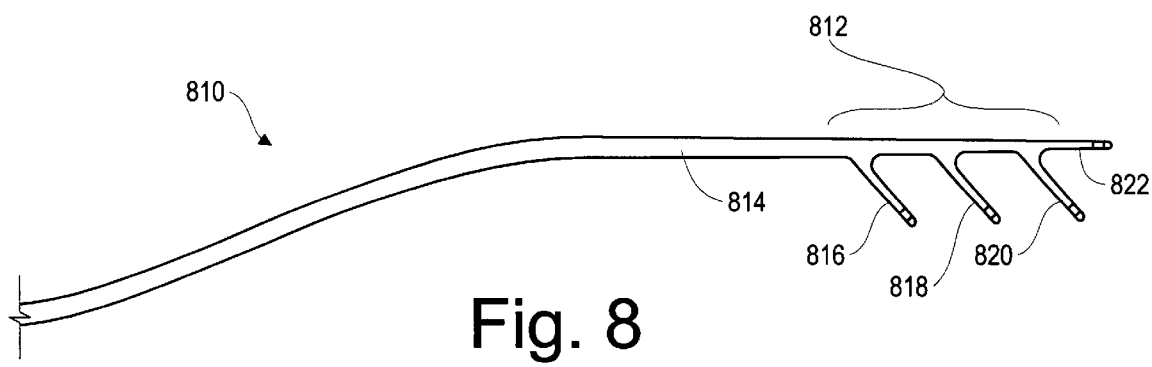
FIG. 8 shows an alternative embodiment of a furcated lead according to the invention having a comb-like asymmetric configuration of distal end segments.

As illustrated in FIG. 1, the junction area 130 is a single body from which all of the distal end segments 114–120 radiate. It should be recognized, however, that other configurations are possible. For example, it may be advantageous to stagger the junction area 130 and the distal end segments (as shown in FIG. 8) to decrease the width of the lead 110 and facilitate insertion through a cannula or other surgical tool. Various other configurations will be illustrated and discussed in greater detail below.

In a presently preferred embodiment of the invention, the lead 110, and particularly the body 132 of the lead 110, has a diameter between approximately 1.0 mm and approximately 1.5 mm. In general, a smaller diameter is better, consistent with sufficient ruggedness and ease of handling.

As shown, the junction area 130 is fabricated from the same silicone material as the lead body 132 and the distal end segments 114–120. However, in one embodiment of the invention, the junction area 130 is further provided with reinforcing members to resist forces acting on the distal end segments 114–120 or the body 132 and to prevent the lead 110 from rupturing or otherwise failing when forces are applied. In one embodiment of the invention, the junction area 130 optionally includes a fan-shaped sheath or web of reinforcing material 136, such as polyester, nylon, or aramid (e.g. KEVLAR®), embedded therein. Such a sheath would be either custom-fabricated, formed from a sheet of material, or woven from fibers, as desired, and is preferably biocompatible. Alternatively, the junction area 130 may include strong fibers of reinforcing material, such as polyester, nylon, or aramid, extending from the body 132, through the junction area 130, and into the distal end segments 114–120. Such a function can also be accomplished with metallic structures used in lieu of polymer fibers. If desired, these metallic structures may be fabricated to spring bias the individual distal end segments 114–120 into a predetermined configuration for ease of use or for other reasons, but it is presently preferred to leave the distal end segments 114–120 unbiased to allow precise and customized positioning with minimal resistance.

Similarly, a lead according to the invention, including a proximal portion, a body 132, a junction area 130, and a plurality of distal end segments 114–120, may be fabricated via any of a number of known methods. For example, prefabricated tubes may be inserted into a prefabricated junction area 130 and fused, a junction area may be molded over a number of prefabricated tubes, or the entire lead assembly may be molded as a single unit (such as by liquid injection molding or compression molding).

It should be recognized that the illustration of FIG. 1 is not to scale, but is intended to illustrate the functional and schematic relationships among the various structures and features of a lead according to the invention as described herein. Each of the distal end segments 114–120 is preferably at least 20 mm in length, allowing and facilitating electrode placement approximately 10 to 30 mm apart near the surface of the brain. It should be appreciated that some or all of the distal end segments may be significantly longer than 20 mm, for example when some or all of the distal electrodes are to be placed in deep brain structures.

Each of the distal end segments 114–120 may be as little as 0.5 mm in diameter, or in some circumstances as wide as 1.0–1.5 mm. A diameter of 0.5 mm is presently preferred as the smallest practical size for manufacturing consistent with sufficient structural integrity and ease of handling for surgical applications. It should be noted, however, that a smaller diameter might be preferable in some applications.

The electrodes 122–128 may vary in size. As is well known in the art of designing physiological sensing and stimulation electrodes, a stimulation electrode's surface area is proportional to the electrical current density (and charge density) delivered by the electrode, and analogously, a sensing electrode's surface area is proportional to its sensitivity to electrographic signals. Accordingly, to minimize departures from the electrical parameters used with traditional strip and grid electrodes, it may be beneficial to provide distal electrodes 112–128 according to the invention with surface areas comparable to those of traditional electrodes.

A standard strip or grid electrode has a surface area of approximately 4 to 15 mm$^2$, with a representative electrode having a surface area of approximately 8 mm$^2$. The latter surface area measurement corresponds to an exposed circular contact surface having a diameter of approximately ⅛ inch (or 3.2 mm). To provide the equivalent surface area on a ring electrode having a diameter of 0.5 mm, an electrode length of approximately 5 mm would be necessary.

For varying neurological sensing and stimulation applications, it is currently believed that electrode surface areas between 0.75 mm$^2$ and 15 mm$^2$ would be advantageous. On a distal end segment having a ring electrode with a diameter of 0.5 mm, an electrode length of 0.5 mm yields a surface area of approximately 0.75 mm$^2$, and on a distal end segment having a ring electrode with a diameter of 1.5 mm, an electrode length of 3 mm yields a surface area of approximately 15 mm$^2$. In any event, it is not necessarily advantageous to match the surface area of electrodes according to the invention with traditional strip, grid, and depth electrodes, particularly when current and charge parameters can be adjusted to compensate. It should be noted, however, that decreasing the surface area of an electrode might, in some circumstances, disadvantageously decrease sensitivity in a sensing application, or fail to stimulate a sufficient population of neurons in a stimulation application. Similarly, increasing the surface area too far might decrease precision in a sensing application and might require a prohibitively high current to be applied in a stimulation application. These considerations are known in the art of medical sensing and stimulation electrode design.

All of the dimensions set forth above are considerably variable, particularly when a lead according to the invention is employed in differing applications. The specific measurements and dimensions provided herein are intended to provide details on a specific exemplary embodiment, and the scope of the invention should not be limited thereby. Additional construction details will be considered below in connection with FIG. 5.

It should further be noted that sensors other than electrodes may be employed on some or all of the distal end segments. For example, a temperature sensor (e.g., a thermocouple), a chemical concentration sensor (such as a dissolved oxygen sensor), or a pressure sensor may be advantageously employed in lieu of one or more of the distal electrodes in some embodiments of the invention.

Figure 2:
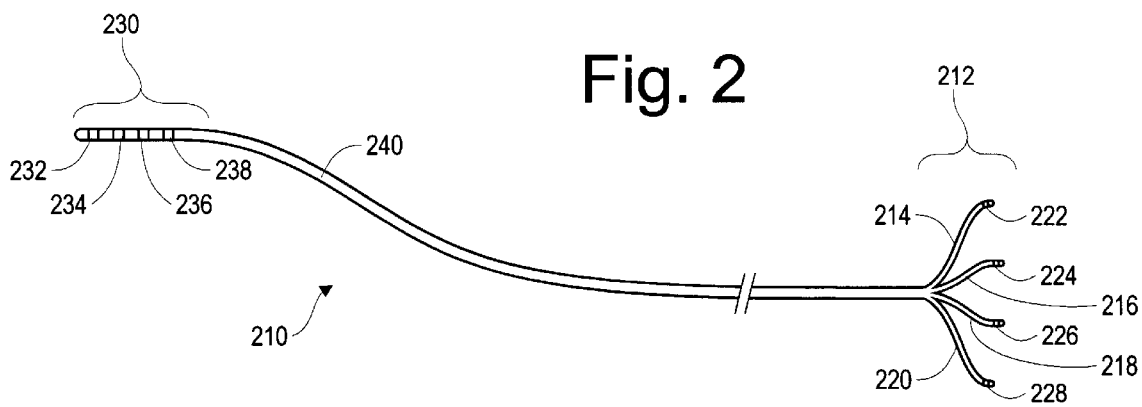
FIG. 2 is a diagram depicting an illustrative furcated lead according to the invention, including proximal and distal portions.

Referring now to FIG. 2, an entire lead 210 according to the invention, in a configuration suitable for use with an implantable neurostimulator, is illustrated. As in FIG. 1, a distal portion 212 includes a plurality of distal end segments 214, 216, 218, and 220 and electrodes 222, 224, 226, and 228, though the specific dimensions and configuration of the distal end segments 214–220 and electrodes 222–228 may differ from the corresponding elements of FIG. 1.

A proximal portion 230 of the lead 210 is illustrated in FIG. 2. The proximal portion 230 is used to attach the lead 210 to a device or some kind of equipment. In various embodiments of the invention, the proximal end may be adapted for implantable use or may be designed for external attachment for short-term inpatient or long-term percutaneous use.

The proximal portion 230 may have a specifically designed lead connection adapter or may simply include separate conductors to attach to a junction block. As illustrated, the proximal portion 230 of FIG. 2 includes four coaxial lead connection terminals 232, 234, 236, and 238, each of which is electrically connected to one of the distal electrodes 222–228 via an electrical conductor extending through the lead 210. Preferably, and as discussed in further detail below, a plurality of helical conductors connect the lead connection terminals 232–238 to the respective distal electrodes 222–228. A helical configuration is favored because of its ability to tolerate longitudinal stretching of the lead 210 without breaking.

In one embodiment of the invention, when the lead 210 is coupled to an implanted neurostimulator via the lead connection area of the proximal portion 230, a suitable overall length for the lead 210 is between approximately 250 and 500 mm. A body portion 240 of the lead 210 has a diameter between approximately 0.5 mm and approximately 2.0 mm, and is preferably between approximately 1.0 mm and approximately 1.3 mm. As explained above, thinner is generally better, consistent with structural integrity, ease of manufacturing, and ease of handling.

In the disclosed embodiment, the four lead connection terminals 232–238 are provided to enable compatibility between the lead 210 and an implantable neurostimulator having a corresponding inline connector. If it is desirable to have additional distal end segments on a lead according to the invention, it should be recognized that it is possible, in an alternative embodiment, to provide a furcated proximal portion to the lead in the same manner that a furcated distal portion is shown in FIGS. 1–2. For example, for an eight-way furcated lead with eight separate distal end segments and electrodes, or a four-way furcated lead with two electrodes on each distal end segment, the proximal portion may be split into two lead connection segments, each having four coaxial lead connection terminals. A single body portion (like the body portion 240 of FIG. 2) would be used two connect the two lead connection segments to the plural distal end segments.

Figure 3:
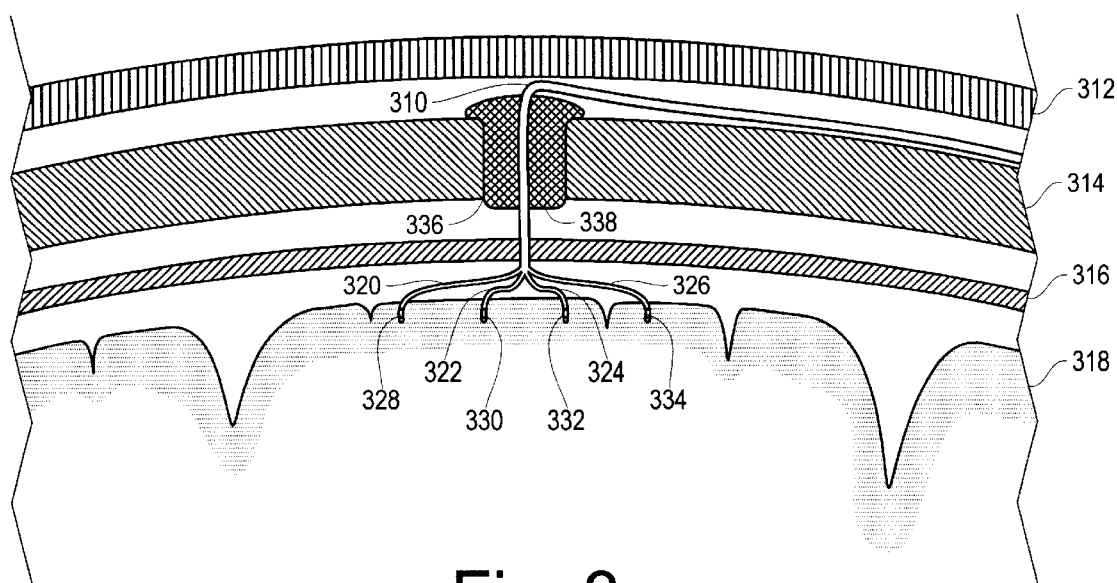
FIG. 3 is an illustration showing the use of a furcated lead according to the invention in an exemplary section of a patient's head, including the patient's brain, dura mater, and cranium.

FIG. 3 depicts a schematic cross section of the anatomy of a patient's head, illustrating an example of how a furcated lead according to the invention may be employed. The drawing of FIG. 3 is not to scale, and is not necessarily intended to represent any particular anatomical features or landmarks.

In general, a furcated lead 310 according to the invention is advantageously situated below a patient's scalp 312, and extends through the patient's cranium 314 and dura mater 316 to access the patient's cortex 318.

As illustrated, and consistent with the illustrations of FIGS. 1–2, the lead 310 has a furcated distal portion including several distal end segments 320, 322, 324, and 326, which are shown inserted into desired electrode sites. Choosing desired electrode sites may be performed at any appropriate stage of the surgical procedure, including presurgically in an operative planning stage; intraoperatively after a craniotomy has been performed or a burr hole has been made; or intraoperatively after one or more other procedures, such as functional mapping, have been performed.

Each of the distal end segments 320–326 is inserted a short distance into the cortex 318, only enough to ensure that electrodes 328, 330, 332, and 334 are fully embedded in neural tissue. This configuration is adapted to serve as a replacement for a strip electrode, with four electrodes 328–334 inserted shallowly in the cortex in an essentially collinear configuration. Other configurations are, of course, possible, and are described elsewhere herein.

The electrodes 328–334 and the distal end segments 320–326 are preferably inserted into the cortex substantially normal to the surface of the brain; this arrangement minimizes tissue damage and orients the electrodes consistently with respect to each other. Consequently, and as depicted somewhat in FIG. 3, the distal end segments 320–326 need to be sufficiently flexible where they exit the cortex to avoid adverse pressure effects on the brain or any portion of the lead 310. In the absence of external forces, the distal end segments will ordinarily remain implanted in the desired electrode sites without any affixation means, but if desired, anchors may be provided at the distal tips of the segments 320–326 to improve retention. Such anchors may take the form of barbs or textured surfaces. However, providing such retention mechanisms would not ordinarily be desirable, since they would potentially adversely impact ease of extraction or repositioning when necessary.

The distal end segments 320–326 are inserted in the cortex 318 through a burr hole 336 defined in the patient's cranium 314 and preferably surgically formed; the lead 310 is anchored within the burr hole 336 by way of a burr hole cover 338 inserted within and affixed to the burr hole 336. The burr hole cover 338 is adapted to hold the lead 310 in place and prevent undesired movement of the distal end segments 320–326, even if forces are applied to other portions of the lead 310. Various configurations of burr hole covers are well known in the art and are commercially available. Alternatively, the lead 310 may be cemented within an access hole.

If there is insufficient space to implant all of the electrodes 328–334 when inserted through a burr hole 336, an alternative approach is to perform a craniotomy and remove, at least temporarily, a larger portion of the patient's cranium 314. A larger incision may also be made in the dura layer 316 to facilitate placement. This arrangement may be maintained for short-term inpatient use of a lead according to the invention, or if long-term use is desired, the removed cranial portion may be replaced and the lead 310 routed through a burr hole or other access hole.

As described above in conjunction with FIG. 2, a proximal end of the lead 310 connects to an implanted neurostimulator (not shown). It may be advantageous to anchor the lead 310 to the patient's cranium 314 at one or more points between the burr hole 336 and the neurostimulator, so that the lead 310 remains in a preferred location under the patient's scalp 312.

Figure 4:
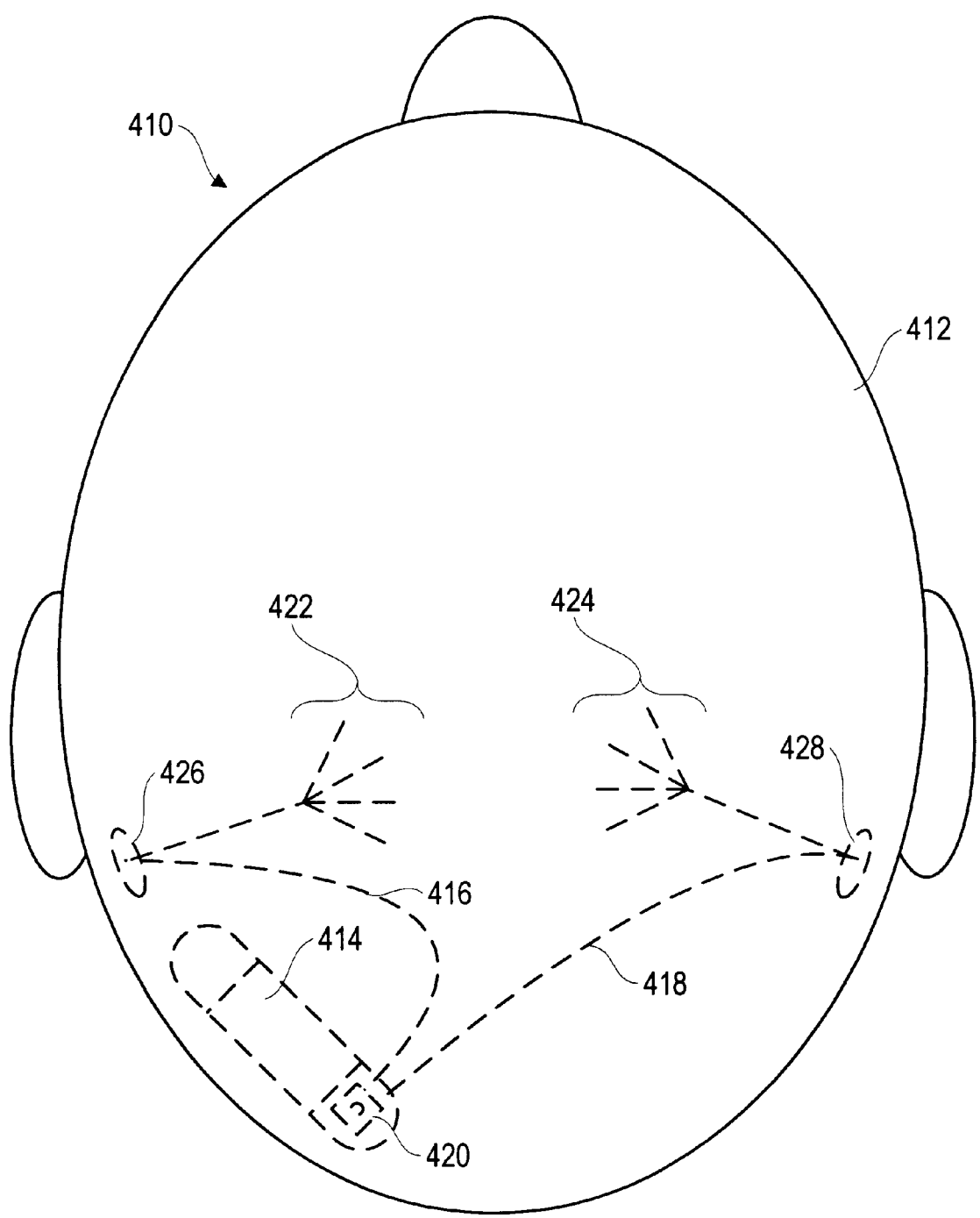
FIG. 4 is a schematic view of an implantable neurostimulator system incorporating a furcated lead according to the invention.

FIG. 4 schematically illustrates an exemplary configuration of an implantable system 410 for the treatment of neurological disorders, as it would be generally situated under the scalp of a patient's head 412 and implanted intracranially. The illustrated embodiment of the system 410 has a control module 414 and two leads 416 and 418 according to the invention, each of which connects a lead connector 420 on the control module 414 to a plurality of distal electrodes 422 and 424, respectively. It is envisioned that the control module 414 is permanently implanted into the patient's cranium in a location where the bone is fairly thick. In an alternative embodiment, it is also envisioned that the control module 414 could be located in the trunk of the patient's body like a heart pacemaker with the connecting wires being run under the patient's skin. Depending on the application, and as described above, the electrodes 422 and 424 would be placed under the cranium and shallowly in the patient's cortex or placed deep into the brain. The connecting leads 416 and 418 are run from the control module 414, underneath the patient's scalp, through burr holes 426 and 428 to the electrodes placed beneath the patient's cranium. Although FIG. 4 shows only four active electrodes 422 on the first connecting lead 416 and four electrodes 424 on the second connecting lead 418, it should be reiterated that more (or fewer) than four active electrodes with connecting conductors may be used with and by leads according to the present invention.

As described above, the leads 416 and 418 carry EEG signals from the electrodes 422 and 424 to the neurostimulator 414. The electrodes 422 and 424 can also be selectively energized by the neurostimulator 414 via the leads 416 and 418 to electrically stimulate the patient's brain. Further information on detection methods, stimulation schemes, and systems adaptable to employ the systems and methods set forth herein are described in detail in U.S. Pat. No. 6,016,449 to Fischell et al., which is incorporated by reference as though set forth in full.

Figure 5:
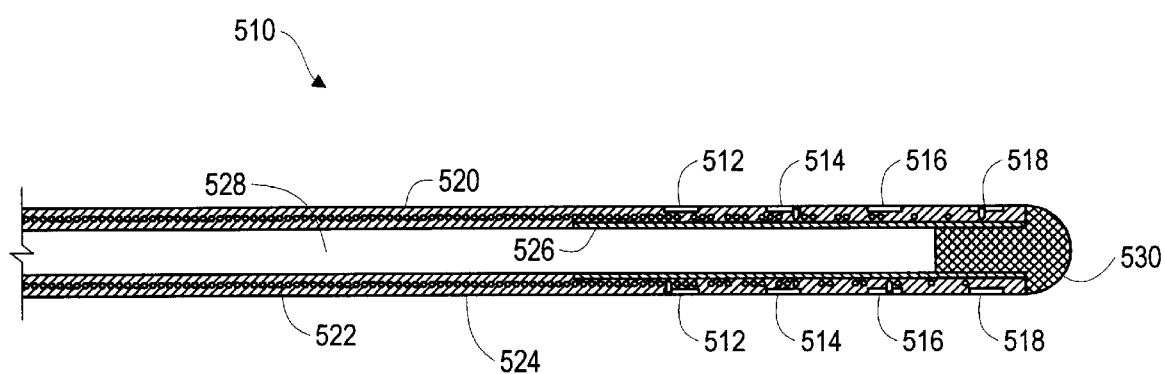
FIG. 5 is a schematic sectional view of a distal end segment of a furcated lead according to the invention.

FIG. 5 illustrates an exemplary longitudinal cross section of a portion of a lead 510 according to the invention. The specific embodiment illustrated in FIG. 5 includes four ring electrodes 512, 514, 516, and 518 on a single distal end segment 520. A furcated lead according to the invention may have two instances of the distal end segment 520, each with four electrodes, for a total of eight electrodes. A proximal lead connector would then include eight terminals, which may all be coaxially arranged on a single lead connection segment, or four terminals may be arranged on two furcated lead connection segments, as described above.

In any case, the embodiment illustrated in FIG. 5 is deemed to be representative of a distal end segment according to the invention, although varying the number of electrodes may vary the illustrated structure in ways that should be apparent. It should be noted that the cross section of FIG. 5 may also be representative of a proximal lead connection segment according to the invention; the construction is preferably similar or identical, though dimensions and some materials may vary.

The distal end segment 520 illustrated in FIG. 5 includes a helically arranged conductor set 522 that includes four conductors, one for each of the electrodes 512–518. Each of the conductors in the conductor set 522 is affixed to and in conductive communication with a respective one of the electrodes 512–518.

The electrodes 512–518 are fabricated as rings of a biocompatible conductive material, preferably platinum or a platinum-iridium alloy. They are arranged around and somewhat embedded into a flexible shaft 524, which preferably is fabricated from silicone or some other flexible, durable, and biocompatible material. A portion of the distal end segment 520 includes a reinforcing tube 526, preferably fabricated from a more rigid polymer material, such as, polyamide, polyimide, or polyetheretherketone (PEEK). Together, the shaft 524 and the tube 526 define a longitudinal lumen 528, which as described above (in connection with FIG. 1) may be employed to receive a stylet to facilitate implantation. A stylet may not always be necessary, though, notably when if the distal end segment 520 is sufficiently rigid from the use of a helical conductor set 522 and/or a reinforcing tube 526.

Although the conductor set 522 is depicted in FIG. 5 as helical, or coiled about the longitudinal axis of the distal end segment 520 to provide some longitudinal resilience, the conductors may alternatively simply extend longitudinally through the distal end segment 520, particularly if there is insufficient space to urge them into a helical configuration, and especially if the reinforcing tube 526 is extended to resist stretching along most or all of the length of the distal end segment 520. The preferred configuration is helical, particularly in the case of a single uninsulated conductor.

The tip of the distal end segment 520 is closed by a relatively rigid plug 530 adapted to fit within the reinforcing tube 526, or if no such tube is present, within the shaft 522. The plug is preferably fabricated from a relatively rigid biocompatible polymer, and is crimped, glued, molded, or fused in place. It should be observed that numerous materials are possible for the plug 530, reinforcing tube 526, the junction area 130 reinforcing members, and any other relatively rigid component of a lead according to the invention. Various categories of polymers and plastics such as polyester, polyimide, polyamide, polyetheretherketone (PEEK), and specific materials falling into those categories such as nylon and aramid (e.g. KEVLAR®), are particularly well suited.

Several exemplary electrode dimensions and locations have been set forth above, but it is appropriate to note that the most distal electrode 518 is positioned as close to the plug 530 as practical, and that the electrodes 512–518 (where more than one electrode is used) are spaced along the distal end segment 520 at any desired interval, but preferably at an approximately 10 mm pitch. Embodiments having multiple electrodes on a single distal end segment are illustrated in FIGS. 6 and 7, described below.

Figure 6:
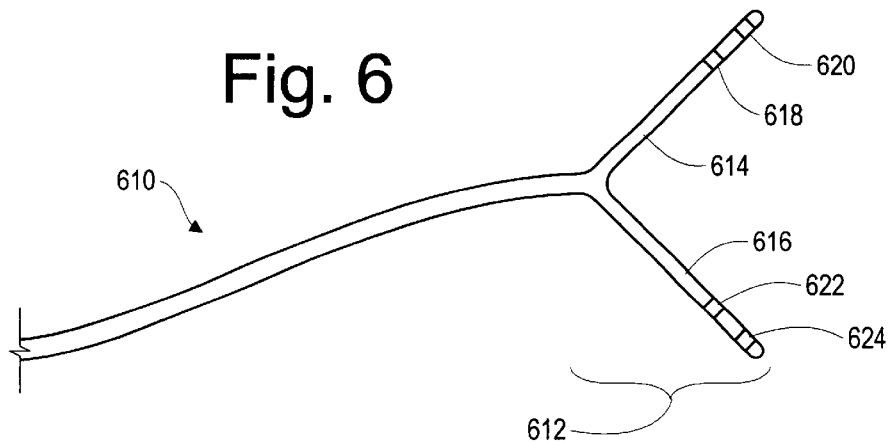
FIG. 6 depicts an alternative embodiment of a furcated lead according to the invention having two distal end segments, each with two electrodes.

FIG. 6 illustrates an alternative embodiment of a lead 610 according to the invention, where a furcated distal portion 612 has two distal end segments 614 and 616, each of which has two electrodes 618 and 620, and 622 and 624, respectively. As illustrated in FIG. 6, each of the distal end segments has a diameter that is comparable to (but slightly thinner than) the diameter of a body portion of the lead 610. Each of the distal end segments 614 and 616 is fabricated in a manner similar to that illustrated in cross section of FIG. 5 (but with only two electrodes, instead of the four electrodes shown in FIG. 5).

Figure 7:
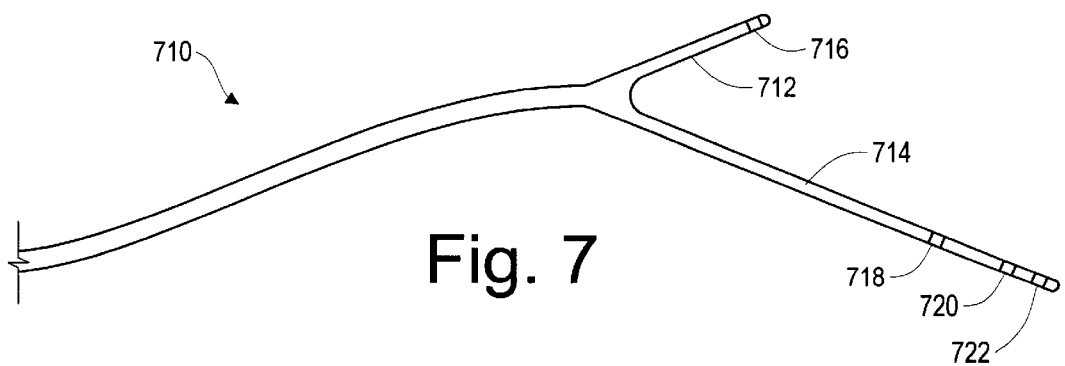
FIG. 7 illustrates an alternative embodiment of a furcated lead according to the invention having two asymmetric end segments with an asymmetric electrode configuration.

As shown in FIG. 7, a lead 710 also having two distal end segments 712 and 714, an asymmetric configuration is possible and may be advantageous in certain applications. A first electrode 716 on a first distal end segment 712 may be adapted for shallow implantation (as shown in FIG. 3), for somatosensory stimulation of the patient's scalp or dura or for some other function outside of the patient's brain, and three other electrodes 718, 720, and 722 may be adapted for deep brain implantation. The illustrated electrodes 718–722 are not evenly spaced, which may be advantageous in some applications. For example, as illustrated, the most proximal electrode 718 of the three may be positioned near the surface of the brain, while the other two electrodes 720 and 722 are positioned in deep brain structures, or alternatively, the most proximal electrode 718 may be used as a common or indifferent electrode positioned away from the other two electrodes 720 and 722, which are embedded in one or more deep brain structures of interest.

FIG. 8 depicts an asymmetric comb-shaped configuration for a lead 810 according to the invention. As illustrated, a junction area 812 between a body portion 814 of the lead 810 and four distal end segments 816, 818, 820, and 822, is staggered and tapered somewhat. A configuration like the one illustrated in FIG. 8 may be advantageous when desired electrode sites are all located in a single direction away from a burr hole or other desired entry point. Also, if the distal end segments 816–822 are sufficiently short, they may be inserted to a desired shallow depth simply by laying the body portion 814 across the surface of the brain and pressing the distal end segments 816–822 into the cortex as far as they will go; other applications may also be envisioned.

It should be observed that while the foregoing detailed description of various embodiments of the present invention is set forth in some detail, the invention is not limited to those details and an implantable medical electrical lead made or used according to the invention can differ from the disclosed embodiments in numerous ways. In particular, it will be appreciated that embodiments of the present invention may be employed in many different applications for sensing or stimulation, not just in the brain. Leads according to the invention may have utility in connection with peripheral nerves, muscles, other portions of the body, and other applications. Hence, the appropriate scope hereof is deemed to be in accordance with the claims as set forth below.

What is claimed is:

1. A furcated medical electrical lead adapted to be at least partially implanted in a human patient, the lead comprising:
   a proximal portion having a lead connection area;
   a furcated distal portion having a plurality of separate distal end segments;
   a body interconnecting the proximal portion and the distal portion; and
   a reinforced integral junction structure situated between and interconnecting the body and the distal portion, wherein the junction structure includes at least one internal reinforcing member,
   wherein each of the separate distal end segments comprises at least one electrode in communication with the lead connection area of the proximal portion.

2. The furcated medical electrical lead of claim 1, wherein the reinforcing member comprises a polymer sheet or web.

3. The furcated medical electrical lead of claim 1, wherein the reinforcing member comprises at least one fiber extending from the body, through the junction structure, and into a distal end segment.

4. The furcated medical electrical lead of claim 1, wherein the reinforcing member comprises at least one metallic structure extending from the body, through the junction structure, and into a distal end segment.

5. The furcated medical electrical lead of claim 4, wherein the metallic structure is configured to bias the plurality of distal end segments into a preferred configuration.

6. The furcated medical electrical lead of claim 1, wherein the junction structure comprises a molded structure integral with the body and the distal end segments.

7. The furcated medical electrical lead of claim 1, wherein the junction structure comprises a prefabricated boot structure configured to receive the body and the distal end segments.

8. The furcated medical electrical lead of claim 1, wherein:
   at least one of the distal end segments defines a longitudinal lumen; and
   wherein the junction structure defines at least one aperture providing stylet access to the longitudinal lumen.

9. The furcated medical electrical lead of claim 8, wherein the aperture is formed as a fluid-resistant septum.

10. The furcated medical electrical lead of claim 1, wherein the body has a diameter between approximately 0.75 mm and approximately 1.5 mm.

11. The furcated medical electrical lead of claim 1, wherein at least one of the distal end segments has a diameter between approximately 0.3 mm and approximately 1.0 mm.

12. The furcated medical electrical lead of claim 1 wherein the body has a diameter and a first distal end segment of the plurality of distal end segments has a diameter, and wherein the diameter of the body is greater than the diameter of the first distal end segment.

13. The furcated medical electrical lead of claim 1, wherein the lead connection area comprises a plurality of inline circumferential terminal rings.

14. The furcated medical electrical lead of claim 1, wherein the lead connection area comprises a furcated structure having a plurality of lead connection members.

15. The furcated medical electrical lead of claim 1, further comprising a conductor connecting the cortical electrode to the lead connection area.

16. The furcated medical electrical lead of claim 15, wherein the conductor is disposed longitudinally within the body and the distal end segment.

17. The furcated medical electrical lead of claim 15, wherein the conductor is arranged in a helical coil within the body and the distal end segment.

18. The furcated medical electrical lead of claim 15, wherein the conductor is arranged in a helical coil within the body and longitudinally in the distal end segment.

19. The furcated medical electrical lead of claim 1, wherein each of the distal end segment further comprises a flexible biocompatible shaft defining a lumen, a relatively rigid tip, and at least one biocompatible conductive electrode.

20. The furcated medical electrical lead of claim 19, wherein the biocompatible conductive electrode comprises a circumferential biocompatible metallic ring.

21. The furcated medical electrical least of claim 19, wherein the biocompatible conductive electrode is fabricated from platinum or a platinum-iridium alloy.

22. The furcated medical electrical lead of claim 19, wherein the biocompatible conductive electrode has a surface area between approximately 0.75 $mm^2$ and approximately 15 $mm^2$.

23. The furcated medical electrical lead of claim 1, wherein one of the distal end segments further comprises a rigidity enhancing tube disposed within at least a portion of the distal end segment.

24. The furcated medical electrical lead of claim 1, wherein the distal end segments are prearranged in a flat fan pattern.

25. The furcated medical electrical lead of claim 1, wherein the distal end segments are arranged in a three-dimensional radial pattern.

26. The furcated medical electrical lead of claim 1, wherein the distal end segments are arranged in an asymmetric rake pattern.

27. The furcated medical electrical lead of claim 1, wherein at least one of the separate distal end segments further comprises a sensor.

28. A method for using a furcated medical electrical lead in conjunction with a neurological diagnostic or treatment apparatus, wherein the lead has a distal portion with a plurality of separate distal end segments, the method comprising the steps of:
   accessing a patient's cortex by forming an opening in the patient's cranium;
   selecting a plurality of electrode sites in the patient's cortex corresponding to the plurality of distal end segments;
   passing the distal portion of the lead through the opening in the patient's cranium;
   inserting the plurality of distal end segments into the respective plurality of electrode sites by manipulating the distal end segments with a stylet; and
   connecting the lead to the neurological diagnostic or treatment apparatus via a lead connection area at a proximal portion of the lead.

29. The method for using a furcated medical electrical lead of claim 28, wherein the neurological diagnostic or treatment apparatus comprises a neurostimulator, an electrographic recorder, or an electrographic analysis unit.

30. The method for using a furcated medical electrical lead of claim 29, wherein the neurological diagnostic or treatment apparatus is an implanted device.

31. The method for using a furcated medical electrical lead of claim 30, wherein the implanted device is implanted intracranially.

32. The method for using a furcated medical electrical lead of claim 28, wherein the step of inserting the plurality of separate distal end segments comprises the steps of:
   placing the stylet into a desired distal end segment;
   manipulating the stylet and the desired distal end segment to insert the distal end segment into an electrode site;
   removing the stylet from the desired distal end segment; and
   repeating the placing, manipulating, and removing steps for each of the separate distal end segments.

33. The method for using a furcated medical electrical lead of claim 28, further comprising the step of anchoring the furcated medical electrical lead to the patient's cranium.

34. The method for using a furcated medical electrical lead of claim 28, further comprising the step of routing the lead under the patient's scalp.

35. The method for using a furcated medical electrical lead of claim 28, wherein at least one electrode site is near a surface region of the patient's brain.

36. The method for using a furcated medical electrical lead of claim 28, wherein at least one electrode site is within a deep region of the patient's brain.

* * * * *